(12) United States Patent
Looker et al.

(10) Patent No.: US 7,217,409 B2
(45) Date of Patent: May 15, 2007

(54) ALKANOIC ACID DERIVATIVES

(75) Inventors: Brian Edgar Looker, Stevenage (GB); Christopher James Lunniss, Stevenage (GB); Alison Judith Redgrave, Stevenage (GB); Derek Peter Reynolds, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 35 days.

(21) Appl. No.: 10/381,116

(22) PCT Filed: Sep. 21, 2001

(86) PCT No.: PCT/GB01/04226

§ 371 (c)(1),
(2), (4) Date: Aug. 6, 2003

(87) PCT Pub. No.: WO02/24623

PCT Pub. Date: Mar. 28, 2002

(65) Prior Publication Data

US 2004/0067202 A1   Apr. 8, 2004

(30) Foreign Application Priority Data

Sep. 22, 2000 (GB) ................... 0023346.0
Jun. 23, 2001 (GB) ................... 0115438.4
Jun. 30, 2001 (GB) ................... 0116059.7

(51) Int. Cl.
*A61K 51/00* (2006.01)
*C07C 53/15* (2006.01)

(52) U.S. Cl. ............. 424/1.13; 514/958; 562/602
(58) Field of Classification Search ................ 424/43, 424/45, 1.13; 562/602; 564/202; 514/958
See application file for complete search history.

(56) References Cited

U.S. PATENT DOCUMENTS 2,623,900 A  12/1952  Hofer ................... 562/470
2,769,838 A * 11/1956  Matter et al. ............ 564/202

(Continued)

FOREIGN PATENT DOCUMENTS

DE           258179          7/1988

(Continued)

OTHER PUBLICATIONS

Grant & Hackh's chemcal dictionary, 1990, 5th ed. p. 16.*

(Continued)

*Primary Examiner*—Taylor Victor Oh
(74) *Attorney, Agent, or Firm*—Alice P. Bradney

(57) ABSTRACT

A method for treating respiratory disorders comprises administering to a patient a pharmaceutical aerosol formulation comprising: (i) a compound of formula (I)

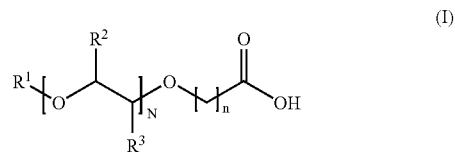

Figure 1:
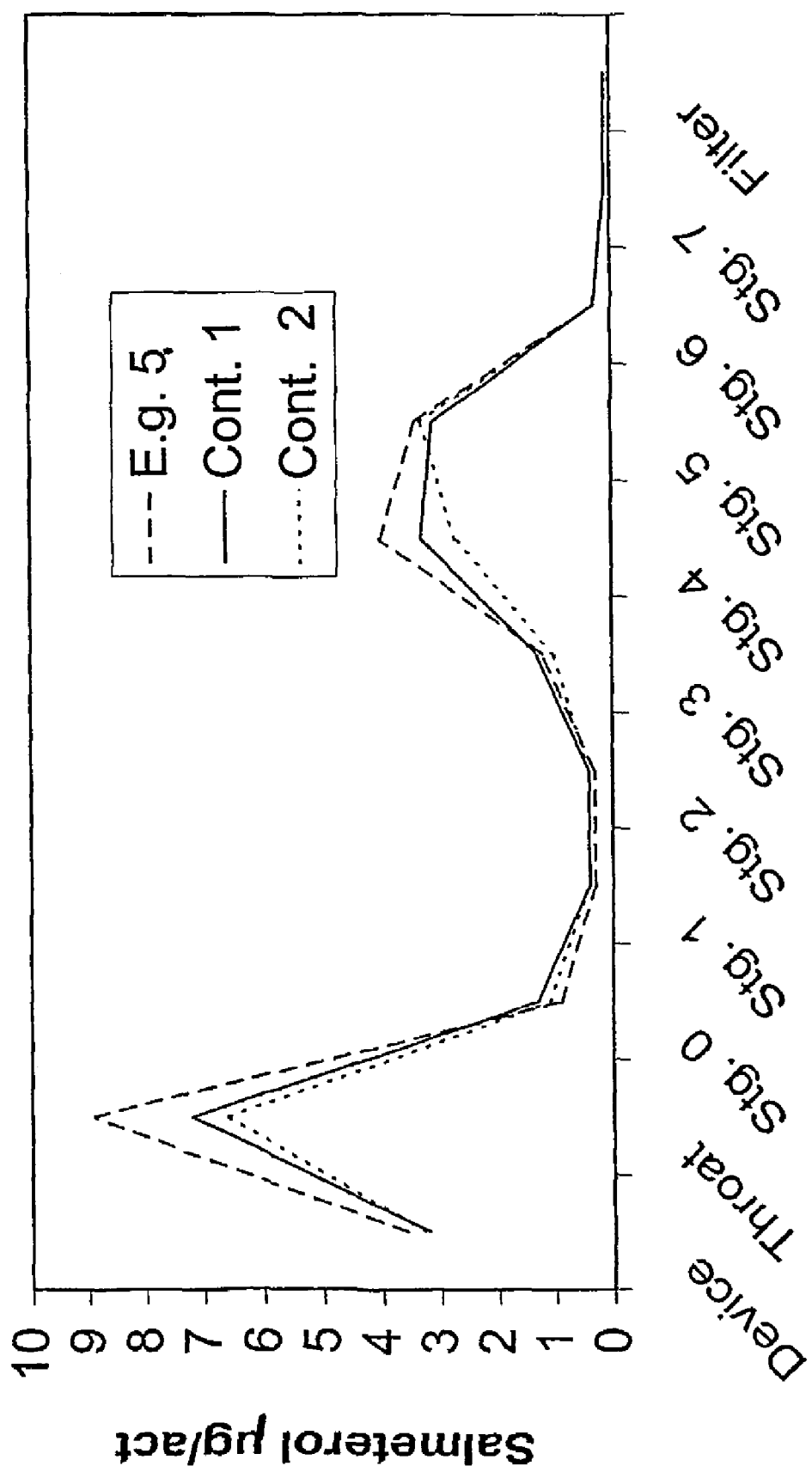

or a salt or solvate thereof, wherein:
n represents an integer 1 to 6;
N represents an integer 1 to 15;
$R^1$ represents $-(CO)_xC_{1-9}$ alkyl or $-(CO)_xC_{1-9}$ fluoroalkyl, which fluoroalkyl moiety contains at least 1 fluorine atom and not more than 3 consecutive perfluorocarbon atoms
wherein x represents 0 or 1; and
$R^2$ and $R^3$ independently represent $C_{1-3}$alkyl or hydrogen, (ii) at least one medicament, and (iii) at least one propellant.

46 Claims, 1 Drawing Sheet

U.S. PATENT DOCUMENTS

| | | | | |
|---|---|---|---|---|
| 4,352,789 | A | 10/1982 | Thiel | 424/46 |
| 5,126,123 | A | 6/1992 | Johnson | 424/45 |
| 5,376,359 | A | 12/1994 | Johnson | 424/46 |
| 5,810,915 | A | 9/1998 | Nagai et al. | 106/31.43 |
| 5,972,082 | A | 10/1999 | Koyano et al. | 106/31.27 |

FOREIGN PATENT DOCUMENTS

| | | |
|---|---|---|
| EP | 0372777 | 6/1990 |
| FR | 7702 | 2/1970 |
| WO | 9104011 | 4/1991 |
| WO | 9111173 | 8/1991 |
| WO | 9111495 | 8/1991 |
| WO | 9114422 | 10/1991 |
| WO | 9200061 | 1/1992 |
| WO | 9200062 | 1/1992 |
| WO | 9609816 | 4/1996 |

OTHER PUBLICATIONS

U.S. Appl. No. 09/580,008.

Bellouard, et. al., "A convenient synthetic route to polyether-tagged cyclam ligands and their nickel derivatives", *European Journal of Organic Chemistry*, 1999, 3257-3261.

Heimann, et. al., "Hydrophile fette hydrophilic lipids", *Liebigs Annalen Der Chemie, Verlag Chemie GMBH*. Weinheim, De, vol. 6, 1980, 858-862.

Haines, "Synthesis of some polyethers from carbohydrate derivatives and related compounds, and their interaction with sodium and potassium cations", *Carbohydrate Research*, vol. 78, 1980, 205-211.

Matsushima, et. al., "Synthesis of novel macrocyclic ether-ester compounds via the intramolecular cyclization of oligoethylene glycol monocarboxymethyl ethers", *Tetrahedron Letters*, No. 36, 1979, 3445-3448.

Strzelbicki, et. al., "Extraction of Zn(II), Cd(II), and Hg(II) by dodecyloligo (oxyethylene) carboxylic acids", *Canadian Journal of Chemistry*, vol. 66, 1988, 1695-1700.

Harada, et. al., "Synthesis and antitumor activity of 9-acyloxyellipticines", *Chemical Pharmaceutical Bulletin*, vol. 45, No. 7, 1997, 1156-1162.

Held, et. al., "Synthesis and preliminary evaluation of a new class of fluorinated amphiphiles designed for in-plane immobilisation of biological macromolecules", *Tetrahedron Letters*, vol. 38, No. 11, 1997, 1937-1940.

Database WPI, Section Ch, Week 200027, Derwent Publications Ltd., London, GB; AN 2000-312984 & JP2000095726A (Kawaken Fine Chem Co. Ltd.), Apr. 4, 2000 abstract.

\* cited by examiner

ALKANOIC ACID DERIVATIVES

This application is filed under 35 U.S.C. § 371 as the U.S. National Phase Application of International Application No. PCT/GB01/04226 filed Sep. 21, 2001 claiming priority from Great Britain Application Nos. 0023346.0 filed Sep. 22, 2000, 0115438.4 filed Jun. 23, 2001 and 0116059.7 filed Jun. 30, 2001, the disclosures of which are incorporated by reference in their entirety.

The use of aerosols to administer medicaments has been known for several decades. Such aerosols generally comprise the medicament, one or more chlorofluorocarbon propellants and either a surfactant or a co-solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is essential that the prescribed dose of aerosol medication delivered from the MDI to the patient consistently meets the specifications claimed by the manufacturer and comply with the requirements of the FDA and other regulatory authorities. That is, every dose dispensed from the can must be the same within close tolerances. Therefore it is important that the formulation be substantially homogenous throughout the administered dose at the time of actuation of the metering valve.

In the case of suspension formulations, to control aggregation of fine particles, and thereby influence the dispersability of the suspension it is well established in the art that fluorinated surfactants may be used to stabilise micronised drug suspensions in fluorocarbon propellants such as 1,1,1,2-tetrafluoroethane (P134a) or 1,1,1,2,3,3,3-heptafluoro-n-propane (P227), see for example U.S. Pat. Nos. 4,352,789, 5,126,123, 5,376,359 U.S. application Ser. Nos. 09/580,008, WO91/11173, WO91/14422, WO92/00062 and WO96/09816.

WO92/00061 discloses non-fluorinated surfactants for use with fluorocarbon propellants. Surprisingly, the applicants have now found that a particular group of novel non-fluorinated and low fluorine content compounds with good surfactant properties may be used to prepare novel aerosol formulations, and can b advantageous in terms of improving the stability of the aerosol formulation by reducing drug deposition, increasing shelf life and the like. In addition the compounds of the invention are adequately soluble in the fluorocarbon or hydrogen-containing chlorofluorocarbon propellants or mixtures thereof, obviating the need to use a polar adjuvant.

Thus, in one aspect the invention provides a compound of the general formula (I)

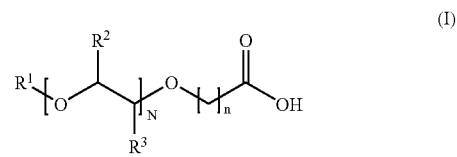

or a salt or solvate thereof, wherein:

n represents an integer 1 to 6;

N represents an integer 1 to 15;

$R^1$ represents $—(CO)_xC_{1-9}$ alkyl or $—(CO)_xC_{1-9}$ fluoroalkyl, which fluoroalkyl moiety contains at least 1 fluorine atom and not more than 3 consecutive perfluorocarbon atoms wherein x represents 0 or 1; and $R^2$ and $R^3$ independently represent $C_{1-3}$alkyl or hydrogen.

Preferably n represents an integer 1 to 4, especially 1. Preferably N represents an integer 1 to 12, especially 2 to 9. Another preferred range for N is 1 to 8, especially 1 to 6, for example, 3 to 6.

Preferably x represents 0.

Examples of group $R^1$ include $—(CH_2)_3CF_2CF_3$, $—CH_2CF_2CF_3$, $—CH_2CF_3$. $—CF_2CF_3$ and $CH_3$.

Preferably $R^1$ represents $—(CO)_xC_{1-5}$ alkyl or $—(CO)_xC_{1-5}$ fluoroalkyl, which fluoroalkyl moiety contains at least 1 fluorine atom and not more than 3 consecutive perfluorocarbon atoms, more preferably $C_{1-3}$alkyl optionally substituted by up to 3 fluorine atoms. Most preferably $R^1$ represents, $—C_{1-3}$alkyl (e.g. methyl, ethyl, propyl or isopropyl), $—CHF_2$, $—CF_3$, or $—CH_2CF_3$, more preferably $—CH_3$, $—CF_3$ or $—CH_2CF_3$, especially $—CH_3$. We also most prefer $R^1$ to represent $—CH_2CF_2CF_3$ or $—CF_2CF_3$. We especially prefer $R^1$ to represent $—CF_2CF_3$ or $—CH_2CF_3$, particularly $—CH_2CF_3$. Another group of compounds of particular interest are those in which $R^1$ represents $C_{1-3}$ fluoroalkyl $C_{0-6}$ alkylene-, particularly $—(CH_2)_3CF_2CF_3$, $—CH_2CF_2CF_3$ or $—CH_2CF_3$.

Perferably $R^2$ and $R^3$ independently represent methyl or hydrogen, more perferably hydrogen.

Suitable salts include alkali metal salts such as sodium and potassium and tertiary alkyl ammonium salts such as tert-butyl ammonium.

Preferably compounds of formula (I) will be present as the free acid.

It will be understood that for N greater than 1, th position of $R^2$ and $R^3$ in each repeating unit need not necessarily be the same, eg they may perhaps be reversed. Nevertheless it is preferred that the respective positions are the same for each repeating unit.

Compounds of formula (I) may contain one or more chiral centres. It will be understood that compounds of formula (I) include all optical isomers of the compounds of formula (I) and mixtures thereof, including racemic mixtures thereof.

In a further aspect the invention provides a pharmaceutical aerosol formulation which comprises particulate medicament, a fluorocarbon or hydrogen-containing chlorofluorocarbon propellant, or mixtures thereof, and a compound of formula (I) as described above.

The compounds of formula (I) employed for the preparation of formulations according to the present invention are effective suspension stabilisers at low concentrations relative to the amount of medicament. Thus, the amount of compound of formula (I) employed is desirably in the range of 0.05% to 20% w/w, particularly 0.5% to 10% w/w, more particularly 0.5% to 5% w/w, relative to the medicament.

The particle size of the particulate (e.g. micronised) medicament should be such as to permit inhalation of substantially all of the medicament into the lungs or nasal cavity upon administration of the aerosol formulation and will thus be less than 100 microns, desirably less than 20 microns, and preferably will have a mass median aerodynamic diameter (MMAD) in the range 1–10 microns, e.g. 1–5 microns.

The final aerosol formulation desirably contains 0.005–10% w/w, preferably 0.005–5% w/w, especially 0.01–1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as sodium salt), ketotifen or nedocromil (e.g. as sodium salt); anti-infectives e.g. cephalosporins, penicillins, streptomycin, sulphonamides, tetracyclines and pentamidine; anti-histamines, e.g. methapyrilene; anti-inflammatories, e.g. beclomethasone (e.g. as dipropionate), fluticasone (e.g. as propionate), flunisolide, budesonide, rofleponide, mometasone furoate, ciclesonide, triamcinolone acetonide or 6α, 9α-difluoro-11β-hydroxy-16α-methyl-3-oxo-17αpropionyloxy-androsta-1,4-diene-17β-carbothioic acid S-(2-oxo-tetrahydro-furan-3-yl) ester; anti-tussives, e.g. noscapine; bronchodilators, e.g. albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol, 4-hydroxy-7-[2-[[2-[[3-(2-phenylethoxy)pro-pyl]sulfonyl]ethyl]amino]ethyl-2(3H)-benzothiazolone; diuretics, e.g. amiloride; anticholinergics, .g., ipratropium (e.g. as bromide), tiotropium, atropine or oxitropium; hormones, e.g. cortisone, hydrocortisone or prednisolone; xanthines, e.g. aminophylline, choline theophyllinate, lysine theophyllinate or theophylline; therapeutic proteins and peptides, e.g. insulin or glucagon. It will be clear to a person skilled in the art that, where appropriate, the medicaments may be used in the form of salts, (e.g., as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant. It will be further clear to a person skilled in the art that where appropriate the medicaments may be used in the form of a pure isomer, for example, R-albuterol or RR-formoterol.

Particularly preferred medicaments for administration using aerosol formulations in accordance with the invention include anti-allergics, bronchodilators and antiinflammatory steroids of use in the treatment of respiratory disorders such as asthma, COPD or rhinitis by inhalation therapy, for example, cromoglycate (e.g. as sodium salt), albuterol (e.g. as free base or the sulphate), salmeterol (e.g. as xinafoate), formoterol (e.g. as fumarate), terbutaline (e.g. as sulphate), reproterol (e.g. as hydrochloride), a beclomethasone ester (e.g. as dipropionate), a fluticasone ester (e.g. as propionate). Salmeterol, especially salmeterol xinafoate, albuterol sulphate, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Thus suitable combinations include bronchodilators (e.g. albuterol or isoprenaline) in combination with an anti-inflammatory steroid (e.g. beclomethasone ester); a bronchodilator in combination with an anti-allergic (e.g. cromoglycate). Exemplary combinations also include: ephedrine and theophylline; fenoterol and ipratropium (e.g. as bromide); isoetharine and phenylephrine; albuterol (e.g. as free base or as sulphate) and beclomethasone ester (e.g. as dipropionate); budesonide and formoterol (e.g. as fumarate) which is of particular interest; and salmeterol (particularly as salmeterol xinafoate) and fluticasone ester (e.g. as propionate) also of particular interest.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds, preferably binary mixtures, with other fluorocarbons or hydrogen-containing chlorofluorocarbons for example $CHClF_2$, $CH_2F_2$ and $CF_3CH_3$. Particularly preferred as propellants are $C_{1-4}$hydrogen-containing fluorocarbons such as 1,1,1,2-tetrafluoroethan ($CF_3CH_2F$) and 1,1,1,2,3,3,3-heptafluoro-n-propane ($CF_3CHFCF_3$) or mixtures thereof. Preferably a single fluorocarbon or hydrogen-containing chlorofluoocarbon is employed as the propellant, for example, 1,1,1,2-tetrafluoroethane (HFA 134a) or 1,1,1,2,3,3,3-heptafluoro-n-propane (HFA 227), especially 1,1,1,2-tetrafluoroethane.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

If desired the propellant may additionally contain a volatile adjuvant such as a saturated hydrocarbon, for example, propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may if desired, be incorporated into the formulations according to the present invention include, for example, $C_{2-6}$aliphatic alcohols and polyols such as ethanol, isopropanol and propylene glycol and mixtures thereof. Preferably ethanol will be employed. In general only small quantities (e.g. 0.05 to 3.0% w/w) of polar adjuvants are required and the use of quantities in excess of 5% w/w may disadvantageously tend to dissolve the medicament. Formulations preferably contain less than 1% w/w, for example, about 0.1% w/w of polar adjuvant. Polarity may be determined, for example, by the method described in European Patent Application Publication No. 0327777.

However as the compounds of formula (I) are adequately soluble in the fluorocarbon or hydrogen-containing chlorofluorocarbon propellant the need to use a polar adjuvant is obviated. This is advantageous as polar adjuvants especially ethanol are not suitable for use with all patient groups. Formulations containing a compound of formula (I) which avoid use of a polar adjuvant are preferred.

In addition to one or more compounds of the general formula (I), the formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

A particularly preferred embodiment of the invention provides a pharmaceutical aerosol formulation consisting essentially of one or more particulate medicament(s), one or more fluorocarbon or hydrogen-containing chlorofluorocarbon propellant(s) and one or more compound(s) of formula (I).

A further embodiment of the invention is a sealed container capable of withstanding the pressure required to maintain the propellant as a liquid, such as a metered dose inhaler, containing therein the aerosol formulation as described above.

The term "metered dose inhaler" or MDI means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

As an aspect of this invention there are also provided processes for the preparation of compounds of formula (I).

Therefore a process for preparing a compound of formula (I) is provided which comprises:

(a) reacting a compound of formula (II)

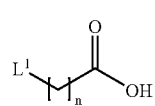

(II)

wherein n is defined above and $L^1$ is a leaving group or a protected derivative thereof, with a compound of formula (III)

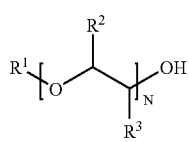

(III)

wherein N, $R^1$, $R^2$ and $R^3$ are defined above; or (b) reacting a compound of formula (IV)

(IV)

wherein n is defined above, or a protected derivative thereof, with a compound of formula (V)

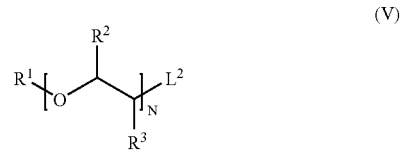

(V)

wherein N, $R^1$, $R^2$ and $R^3$ are defined above and $L^2$ is a leaving group; or (c) reacting a compound of formula (VI)

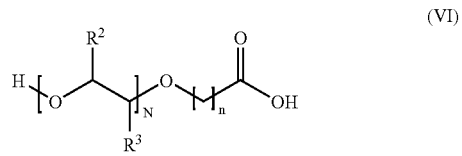

(VI)

wherein n, N, $R^2$ and $R^3$ are defined above, or a protected derivative thereof, with a compound of formula (VII)

(VII)

wherein $R^1$ is defined above and $L^3$ is a leaving group; or (d) reacting a compound of formula (VIII)

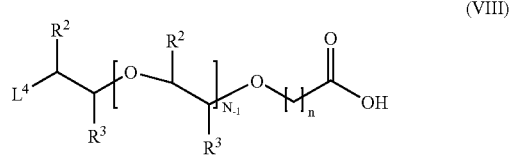

(VIII)

wherein n, N, $R^2$ and $R^3$ are defined above and $L^4$ is a leaving group with a compound of formula (IX)

(IX)

wherein $R^1$ is defined above; or (e) oxidising a compound of formula (X)

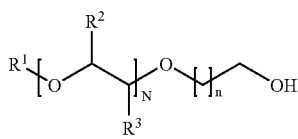

wherein n, N, R$^1$, R$^2$ and R$^3$ are defined above, to give the corresponding acid or a salt or solvate thereof; or (f) deprotecting a protected compound of formula (I).

A further process for preparing a compound of formula (I) is provided which comprises:

(g) preparing a compound of formula (I) wherein x is 1 by reacting a compound of formula (VI) as defined above, or a derivative thereof wherein the carboxylic acid group is protected, with an acid of formula (XI)

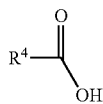

or a salt or solvate thereof or a derivative thereof (such as an anhydride including a mixed anhydride or an acid chloride) wherein R$^4$ represents —C$_{1-9}$ alkyl or a —C$_{1-9}$ fluoroalkyl moiety which contains at least 1 fluorine atom and not more than 3 consecutive perfluorocarbon atoms; or (h) preparing a compound of formula (I) wherein x is 1 by reacting a compound of formula (VIII) as defined above or a protected derivative thereof wherein the carboxylic acid group is protected with an acid of formula (XI) or a salt or solvate thereof.

In process (a), (b), (c) and (d) the carboxylic acid is preferably protected for example, as an ester such as a C$_{1-4}$alkyl ester or a benzyl ester. The process above will usually be performed in the presence of a strong non-nucleophilic base, for example, tert-butoxide such as potassium tert-butoxide or lithium diisopropylamine in an inert solvent, for example, toluene or dimethylformamide (DMF), at temperatures in the range 0 to reflux. Preferably potassium tert-butoxide will be used as the base and toluene will be used as the solvent, preferably at reflux. Suitable leaving groups L$^1$ L$^2$, L$^3$ and L$^4$ include halogen, especially bromine.

In process (e) methods for oxidising a primary alcohol to the corresponding carboxylic acid, using strong oxidising agents are well known to persons skilled in the art. Suitable reagents include: chromic acid, permanganate, for example, potassium permanganate, and nitric acid. Permanganate is preferred for use in process (e), especially potassium permanganate.

In process (f), examples of protecting groups (e.g. for carboxylic acids) and means for their removal can be found in "Protecting Groups In Organic Synthesis" by Theodora Green and Peter G. M Wuts (John Wiley and Sons Inc 1999). Suitable carboxylic acid protecting groups include but are not limited to carboxylic acid esters, for example, ethyl ester, aryl esters e.g. benzyl ester.

Protecting groups can be removed by acid or base catalysed hydrolysis or reduction for example, by hydrogenation. Where the carboxylic acid is protected as the benzyl ester, the protecting group may be removed for example by hydrogenation. Where the carboxylic acid is protected as the C$_{1-4}$alkyl ester, the protecting group may be removed for example by base hydrolysis.

Methods of esterifying acids are well know to person skilled in the art. Process (g) may be performed in an inert solvent at a non-extreme temperature under acidic conditions. Preferably the carboxylic acid moiety in the compound of formula (VI) will be protected e.g with a group mentioned above in relation to process (f). The reaction may be encouraged to be more efficient by, for example, the presence of a water scavenger such magnesium sulphate or molecular sieves.

Process (h) may be performed in an inert solvent at a non-extreme temperature in the presence of a sterically hindered or non-nucleophilic base, for example, triethylamine or Hunig's base. Preferably the carboxylic acid moiety in the compound of formula (VIII) will be protected.

Compounds of formula (VI) may be prepared by a process comprising:

(i) reacting a compound of formula (IV) as defined above, or a protected derivative thereof, with a compound of formula (XII)

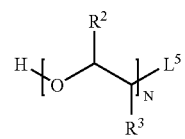

wherein N, R$^2$ and R$^3$ are as defined above and L$^5$ is a leaving group (such as one mentioned above), or a protected derivative thereof; or (ii) reacting a compound of formula (II) as defined above, or a protected derivative thereof, with a compound of formula (XIII)

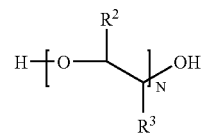

wherein N, R$^2$ and R$^3$ are as defined above, or a derivative thereof wherein the non-reacting hydroxyl is protected.

Compounds of formula (VIII) may be prepared by a process comprising:

(i) reacting a compound of formula (IV) as defined above, or a protected derivative thereof, with a compound of formula (XIV)

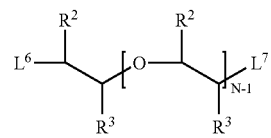

wherein N, R$^2$ and R$^3$ are as defined above, L$^6$ is a potential leaving group and L$^7$ is a leaving group; or (ii) reacting a compound of formula (II) as defined above, or a protected derivative thereof, with a compound of formula (XV)

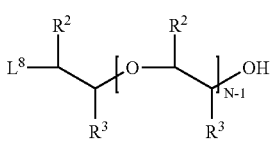

wherein N, $R^2$ and $R^3$ are as defined above and $L^8$ is a potential leaving group.

$L^6$ and $L^8$ are potential leaving groups which may, for example, be protected hydroxyl groups which can be selectively deprotected and converted into good leaving groups by treatment with a halogenating agent such as carbon tetrabromide and triphenylphosphine or phosphorus pentachloride or by treatment with methane sulphonyl chloride or paratoluene sulphonyl chloride to give a compound of formula (VIII).

Compounds of formula (X) may be prepared by a process comprising:
(i) reacting a compound of formula (XVI)

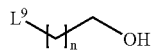

wherein n is defined above and $L^9$ is a leaving group (such as one mentioned above) or a derivative wherein the hydroxyl is protected, with a compound of formula (III) as defined above; or
(ii) reacting a compound of formula (XVII)

wherein n is defined above, or a derivative thereof wherein the non-reacting hydroxyl is protected, with a compound of formula (V) as defined above.

Steps (i) and (ii) in the preparation of compounds of formula (VI), (VIII) and (X) may be performed under condition analogous to those described above for processes (a), (b), (c) and (d) above.

Compounds of formula (XI) may be prepared by oxidising a compound of formula (XVIII)

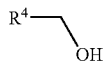

wherein $R^4$ is as defined above.

Suitable conditions include those described above for process (e).

Compounds of formula (VII), (IX), (XI), (XVI), (XVII) and (XVIII) are known or can be prepared by known methods.

Compounds of formula (II), (III), (IV), (V), (XII), (XIII), (XIV) and (XV) may be prepared by methods analogous to those described above or by known methods.

It will be clear to a person skilled in the art that an oxirane such as ethylene oxide or propylene oxide may be used to build up a number of ether monomer units especially where the units have substituents $R^2$ and $R^3$ independently selected from hydrogen and methyl.

Certain compounds of formula (III), (V), (VI), (VII), (X), (XII) (XIII), (XIV) and (XV) are new and form an aspect of the invention.

In addition processes for preparing formulations including one or more compounds of formula (I) form an aspect of this invention.

The formulations of the invention may be prepared by dispersal of the medicament and a compound of formula (I) in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the, emitted dose in pressurised inhalations using apparatus A" as defined in British Pharmacopaeia 1988, pages A204–207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example, aluminum or an alloy thereof which may optionally be anodised, lacquer-coated and/or plastic-coated (e.g. incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO/96/32099). Preferably the canister is fitted with a cap assembly, wherein a drug metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

A further aspect of this invention comprises a process for filling the said formulation into MDIs.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminum can to form an empty canister. The particulate medicament is added to a charge vessel and liquified propellant is pressure filled through the charge vessel into a manufacturing vessel, together with liquified propellant containing the surfactant. The drug suspension is mixed before recirculation to a filling machine and an aliquot of the drug suspension is then filled through the metering valve into the canister.

In an alternative process, an aliquot of the liquified formulation is added to an open canister under conditions which are sufficiently cold to ensure formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channeling device prior to use to form a metered dose inhaler system for administration of the medicament into the lungs or nasal cavity of a patient. Metered dose inhalers are designed to deliver a fixed unit dosage of medicament per actuation or "puff", for example, in the range of 10 to 5000 micrograms of medicament per puff.

Administration of medicament may be indicated for the treatment of mild, moderate, severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example, from 1 to 8 times per day, giving for example 1, 2, 3 or 4 puffs each time.

Suitable daily doses, may be, for example, in the range 50 to 200 micrograms of salmeterol, 100 to 1000 micrograms of albuterol, 50 to 2000 micrograms of fluticasone propionate or 100 to 2000 micrograms of beclomethasone dipropionate, depending on the severity of the disease.

Thus, for example, each valve actuation may deliver 25 micrograms of salmeterol, 100 micrograms of albuterol, 25, 50, 125 or 250 micrograms of fluticasone propionate or 50, 100, 200 or 250 micrograms of beclomethasone dipropionate. Doses for Seretide™, which is a combination of salmeterol (eg as xinafoate salt) and fluticasone propionate, will usually be those given for the corresponding individual component drugs. Typically each filled canister for use in a metered dose inhaler contains 60, 100, 120, 160 or 240 metered doses or puffs of medicament.

An appropriate dosing regime for other medicaments will be know or readily available to persons skilled in the art.

The use of the compounds of formula (I) as described above especially in the preparation of a pharmaceutical formulation; use of a formulation as described above in inhalation therapy, for example, for the treatment or prophylaxis of respiratory disorders; and use of a metered dose inhaler system in the treatment or prophylaxis of respiratory disorders are all alternative aspects of this invention.

A still further aspect of the present invention comprises a method of treating respiratory disorders such as, for example, asthma, which comprises administration by inhalation of an effective amount of a formulation as herein described.

The following non-limiting examples serve to illustrate the invention.

EXAMPLES

The mass spectra were recorded on a HP5989A Engine Mass Spectrometer using thermospray positive ion mode.

The solvent system used for TLC was 10% methanol/1% ammonia in dichloromethane. Where organic solutions were dried during work up magnesium sulphate was used unless specified otherwise.

LCMS was conducted on a Supelcosil LCABZ+PLUS column (3.3 cm×4.6 mm ID) eluting with 0.1% HCO$_2$H and 0.01M ammonium acetate in water (solvent A), and 0.05% HCO$_2$H and 5% water in acetonitrile (solvent B), using the following elution gradient 0–0.7 min 0% B, 0.7–4.2 min 0–100% B, 4.2–5.3 min 100% B, 5.3–5.5 min 100–0%B at a flow rate of 3 mL/min.

GC was conducted on a methyl silicone column 25 m×0.25 mm×0.25 um HP1 or equivalent. The carrier gas was helium at a flow rate of 1 mL/min. The injection volume was 1 µL and the injector temperature was 250° C. with a split injection ratio of 50:1. The septum purge was 2 mL/min. Oven temperature program: initial temperature 150° C. ramp at 10° C./min to 300° C. then hold at 300° C. for 30 mins. The flame ionisation detector was at 300° C. with nitrogen make up gas at 30 mL/min.

Example 1

2,5,8,11-Tetraoxatridecan-13-oic acid (a) Ethyl 2,5,8,11-tetraoxatridecan-13-oate To a stirred solution of triethyl glycol monomethyl ether (3 g) in toluene (100 mL) was added potassium tert-butoxide (2.88 g) and the reaction was stirred at 20° C. for 30 minutes. Ethyl bromoacetate (4.05 g) was added and th reaction was heated at reflux for 19 hours. The reaction was cooled to 20° C. and the solvent was removed in vacuo. The residue was partitioned between water (200 mL) and dichloromethane (200 mL). The organic layer was dried and the solvent was removed in vacuo. Purification by chromatography on silica gel (Biotage), eluting with 50% ethyl acetate in cyclohexane gave the title compound as a clear oil (1.5 g). Mass spectrum 268 m/z [MNH$_4^+$]

(b) 2,5,8,11-Tetraoxatridecan-13-oic acid

The product of step (a) (1.5 g) was stirred in a sodium hydroxide solution (0.1M, 30 mL) for 5 hours. The reaction mixture was adjusted to pH 2 by the addition of hydrochloric acid (2M) and then diluted with brine (300 mL). This was extracted with dichloromethane (2×300 mL) and the combined organic layers were dried and the solvent was removed in vacuo. Purification by chromatography on silica gel (Biotage), eluting with 10% methanol in dichloromethane gave the title compound as a clear oil (900 mg).

Mass spectrum 240 m/z [$MNH_4^+$] $R_f$ 0.15

Other compounds which may be prepared by methods analogous to those given for Example 1 above:

Example 2

2,5,8,11,14,17,20-Heptaoxadocosan-22-oic acid

Clear oil. Mass spectrum 372 m/z [$MNH_4^+$] $R_f$ 0.28

Example 3

2,5,8,11-Tetraoxahexadecan-16-oic acid

Clear oil. Mass spectrum 282 m/z [$MNH_4^+$] $R_f$ 0.35

Example 4

2,5,8,11,14,17,20-Heptaoxapentacosan-25-oic acid

Clear oil. Mass spectrum 414 m/z [$MNH_4^+$] $R_f$ 0.25

Example 5

23,23,23-Trifluoro-3,6,9,12,15,18,21-heptaoxatricosan-1-oic acid (a) 1-Phenyl-2,5,8,11,14,17-hexaoxanonadecan-19-ol To a stirred suspension of sodium hydride (50% dispersion in mineral oil, 2.55 g) in tetrahydrofuran (100 mL) was added hexaethylene glycol (25 g). The reaction mixture was stirred at 5–15° C. for 10 minutes, then benzyl bromide (16.66 g) was added. The suspension was allowed to stand at 20° C. for 72 hours then the reaction mixture was diluted with water (250 mL) and extracted with cyclohexane (250+ 125 mL). Aqueous sodium chloride solution (15% w/w, 300 mL) was added to the aqueous phase and the resulting solution was extracted with ethyl acetate (3×250 mL). The combined ethyl acetate extracts were concentrated in vacuo to give the title compound as an orange oil (18.68 g). LC retention time 2.50 mins. Mass spectrum m/z 390 [$MNH_4^+$]

(b) 19-Phenyl-3,6,9, 12,15,18-hexaoxanonadec-1-yl 4-methylbenzenesulfonate

To a stirred solution of the product of step (a) (1 g) in dichloromethane (20 mL), p-toluenesulfonyl chloride (0.66 g) and triethylamine (0.5 mL) were added and the reaction was stirred at 20° C. for 24 hours. The reaction mixture was diluted with dichloromethane (100 mL) then washed with water (100 mL) and brine (100 mL), dried and the solvent removed in vacuo. Purification by column chromatography on silica gel (Biotage), eluting with 10% ethyl acetate in cyclohexane to give the title compound (1 g). LC retention time 3.37 mins. Mass spectrum m/z 544 [$MNH_4^+$]

(c) 22,22,22-Trifluoro-1-phenyl-2,5,8,11,14,17,20-heptaoxadocosane

To a stirred solution of trifluoroethanol (0.1 g) and sodium hydride (60% dispersion in mineral oil, 0.05 g) in tetrahydrofuran (10 mL) was added the product of step (b) (0.5 g) and the reaction was stirred for 24 hours at 20° C. The reaction was quenched by the addition of methanol (5 mL) and the solvent was removed in vacuo. The residue was partitioned between ethyl acetate (50 mL) and water (50 mL). The organic layer was washed with brine (50 mL), dried and the solvent removed in vacuo. Purification by column chromatography on silica gel (Biotage), eluting with 50% ethyl acetate in cyclohexane to give the title compound (0.27 g). LC retention time 3.17 mins Mass spectrum m/z 472 [$MNH_4^+$]

(d) 20,20,20-Trifluoro-3,6,9,12,15,18-hexaoxaicosan-1-ol

A stirred solution of the product of step (c) (16 g) and 10% palladium on carbon (1 g) in acetic acid:ethanol (1:1, 150 mL) was placed under an atmosphere of hydrogen at 20° C. for 24 hours. The reaction mixture was filtered through a pad of celite and the solvent was removed in vacuo to give the title compound (11 g). Mass spectrum m/z 382 [$MNH_4^+$]

(e) Ethyl 23,23,23-trifluoro-3,6,9,12,15,18,21-heptaoxatricosan-1-oate

To a stirred solution of the product of step (d) (1.5 g) in toluene (30 mL) was added potassium tert-butoxide (0.69 g) and the resulting mixture was stirred at room temperature for 3 hours. Ethyl bromoacetate (1.38 g) was added and the reaction was stirred at 130° C. for 48 hours. The solvent was removed in vacuo and the residue was dissolved in dichloromethane (500 mL) and washed with water (2×400 mL). The organic layer was washed with brine (300 mL), dried and the solvent was removed in vacuo. The residue was purified by column chromatography on silica gel (Biotage), eluting with 65–75% ethyl acetate in cyclohexane to give the title compound as a brown oil (0.40 g). LC retention time 2.77 min. Mass spectrum m/z 468 [$MNH_4^+$]

(f) 23,23,23-Trifluoro-3,6,9,12,15,18,21-heptaoxatricosan-1-oic acid

The product of step (e) (400 mg) was dissolved in an aqueous sodium hydroxide solution (0.1M, 10 mL) and the reaction was stirred at 20° C. for 16 hours. The reaction mixture was acidified to pH 2 by the addition of hydrochloric acid (2M), then this was diluted with brine (200 mL) and extracted with dichloromethane (2×200 mL). The combined organic layers were dried and the solvent was removed in vacuo to give the title compound as a colourless oil (330 mg). LC retention time 2.41 mins. Mass spectrum m/z 440 [$MNH_4^+$]

Example 6

{[2-({2-[(2,2,2-Trifluoroethyl)oxy]ethyl}oxy)ethyl]oxy}acetic acid

The compound was made by an analogous method to Example 5. Clear oil. LC retention time 2.15 mins. Mass spectrum m/z 245 [$M^-$]

Example 7

2,5,8,11,14,17,20,23,26,29-Decaoxahentriacontan-31-oic acid

(a) 2-[2-(2-Methoxyethoxy)ethoxy]ethyl 4-methylbenzenesulfonate

A solution of triethylene glycol monomethyl ether (300 g) in tetrahydrofuran (550 mL) was added dropwise over 105 minutes to a stirred aqueous sodium hydroxide solution (2M, 1.28 L) at 0–5° C. A solution of p toluenesulphonyl chloride (383 g) in tetrahydrofuran (600 mL) was then added to the reaction mixture over 150 minutes, maintaining the temperature at 0–9° C. The reaction mixture was stirred at 0–5° C. for a further 2 hours and then allowed to warm to 20° C. and stirred for 16 hours. Additional aqueous sodium hydroxide solution (2M, 90 mL) was then added slowly to the reaction mixture and stirring was continued for a further 1 hour. Water (1 L) was added to the reaction mixture which was then extracted with toluene (2×1.8 L). The combined organic extracts were washed with water (3×1.8 L) and then concentrated in vacuo to give the title compound as a colourless oil (448 g). GC retention time 11.2 mins

(b) 1-Phenyl-2,5,8,11,14,17-hexaoxanonadecan-19-ol

To a stirred mixture of hexaethylene glycol (10 g), benzyl bromide (4.53 mL) and diisopropyl ether (25 mL) was added tetrahydrofuran (10 mL). The mixture was cooled to 15–20° C. and aqueous sodium hydroxide (10.8M, 4.92 mL) was added slowly maintaining the temperature at 15–20° C. during addition. The resulting mixture was allowed to warm to 20° C. and stirred for a further 17 hours. Water (50 mL) was then added to the reaction mixture, which was then washed with diisopropyl ether (25 mL). Sodium chloride (10 g) was added to the aqueous phase which was extracted with ethyl acetate (3×25 mL). The combined ethyl acetate extracts were dried ($Na_2SO_4$) and concentrated in vacuo to give the title compound as a mobile oil (6.29 g). GC retention time 14.2 mins

(c) 1-Phenyl-2,5,8,11,14,17,20,23,26,29-decaoxatriacontane

To a stirred solution of the product of step (b) (25 g) in tetrahydrofuran (500 mL) at −20° C. was added a solution of potassium tert-butoxide in tetrahydrofuran (1.61M, 50 mL) over 1 hour, maintaining the temperature at about −20° C. The reaction mixture was stirred for a further 15 minutes then a solution of the product of step (a) (29.7 g) in tetrahydrofuran (100 mL) was added over 90 minutes, maintaining the temperature at about −20° C. After stirring at −20° C. for a further 3 hours, the mixture was allowed to warm to 20° C. and stirred for 16 hours. Water (125 mL) was then added and the resultant mixture was concentrated in vacuo to 140 mL. Sodium chloride (12.5 g) was added to the stirred concentrate, which was then washed with diisopropyl ether (4×125 mL). The aqueous phase was diluted with water (50 mL) and extracted with dichloromethane (3×125 mL). The combined dichloromethane extracts were concentrated in vacuo to give the title compound as an orange-brown oil (27.93 g). GC retention time 21.8 mins

(d) 2,5,8,11,14,17,20,23,26-Nonaoxaoctacosan-28-ol

A solution of product from step (c) (13.56 g) in ethyl acetate (68 mL) was stirred under a hydrogen atmosphere with 5% palladium on carbon (1.36 g, wet paste) for 3 hours. The catalyst was then removed by filtration and the filtrate was concentrated in vacuo to give the title compound as a pale yellow oil (10.93 g). GC retention time 15.2 mins

(e) 2,5,8,11,14,17,20,23,26,29-Decaoxahentriacontan-31-oic acid

To a stirred solution of the product of step (d) (20 g) in dry tetrahydrofuran (500 mL) at 0° C. was added sodium hydride (60% dispersion in mineral oil, 2.43 g) portionwise. The reaction was stirred at 0° C. for 30 minutes then ethyl bromoacetate (8.19 g) was added dropwise and the reaction was allowed to warm to 20° C. and stirred for a further 3 hours. Ethanol (100 mL) was then added and stirring was continued at 20° C. for 30 minutes. Sodium hydroxide solution (2M, 100 mL) was then added and the resulting mixture was stirred at 20° C. for 2 hours. The reaction mixture was then partitioned between dichloromethane (700 mL) and water (700 mL). The aqueous layer was acidified to pH 1 by the addition of hydrochloric acid (2M) and then extracted with dichloromethane (3×500 mL). The combined organic layers were dried and the solvent removed in vacuo. Purification by chromatography on silica gel (Biotage), eluting with 10% methanol/1% ammonia (specific gravity 0.880) in dichloromethane gave the title compound as a pale yellow oil (15 g). LC retention time 2.18 mins. Mass spectrum m/z 485 [$M^+$]

Example 8

25,25,26,26,26-Pentafluoro-3,6,9,12,15,18,21-heptaoxahexacosan-1-oic acid

Prepared by a method analogous to Example 5.
Pale yellow oil. LC retention time 2.92 mins. Mass spectrum m/z 518 [$MNH_4^+$]

Example 9

(2-{2-[(4,4,5,5,5-Pentafluoropentyl)oxy]ethoxy}ethoxy)acetic acid

Prepared by a method analogous to Example 5 Pale yellow oil. LC retention time 2.85 mins. Mass spectrum m/z 323 [$M^-$]

Example 10

{2-[2-(2,2,3,3,3-Pentafluoropropoxy)ethoxy]ethoxy}acetic acid

Prepared by a method analogous to Example 5 Pale yellow oil. LC retention time 2.64 mins. Mass spectrum m/z 295 [$M^-$]

Example 11

23,23,24,24,24-Pentafluoro-3,6,9,12,15,18,21-heptaoxatetracosan-1-oic acid

Prepared by a method analogous to Example 5 Pale yellow oil. LC retention time 2.77 mins. Mass spectrum m/z 471 [$M^-$]layers were washed with water (20 mL) and concentrated in vacuo. Purification by chromatography on silica gel (Biotage), eluting with 1.5% methanol in dichloromethane gave the title compound (2.7 g). LC retention time 3.44 mins b) 31,31,31-Trifluoro-1-phenyl-2,5,8,11,14,17,20,23, 26,29-decaoxahentriacontane 20,20,20-Trifluoro-3,6,9,12,15,18-hexaoxaicosan-1-ol (synthesised in example 5(d) above) (1.15 g) and sodium hydride (60% dispersion in mineral oil, 190 mg) were suspended in tetrahydrofuran (20 mL) and stirred for 30 minutes. The product of step (a) (1.25 g) was added and the reaction stirred for a further 15 hours. Additional quantities of both sodium hydride (60 mg) and product of step (a) (625 mg) were added and the reaction stirred for a further 4 hours. Methanol (2 mL) was added and the reaction stirred for 30 minutes and then concentrated in vacuo. The residue was partitioned between dichloromethane (200 mL) and water (200 mL). The organic layer was collected and concentrated in vacuo. Purification by chromatography on silica gel (Biotage), eluting with cyclohexane:ethyl acetate 2:1 to remove the tosylate derivative and then 2.5% methanol in dichloromethane gave the title compound (0.97 g). LC retention time 3.13 mins c) 29,29,29-Trifluoro-3,6,9,12,15,18,21,24,27-nonaoxanonacosan-1-ol

A stirred solution of the product of step (b) (0.97 g) and 10% palladium on carbon (100 mg) in acetic acid:ethanol (1:9, 20 mL) was placed under an atmosphere of hydrogen at 20° C. for 2 hours. The reaction mixture was filtered through a pad of celite and the solvent was removed in vacuo to give the title compound (780 mg). LC retention time 2.45 mins d) 32,32,32-Trifluoro-3,6,9,12,15,18,21,24,27,30-decaoxadotriacontan-1-oic acid To a stirred solution of the product of step (c) (750 mg) in tetrahydrofuran (15 mL) was added sodium hydride (60% dispersion in mineral oil, 91 mg). The reaction was stirred at 20° C. for 30 minutes then ethyl bromoacetate (335 µl) was added and the reaction was stirred for a further 15 hours. Ethanol (1 mL) was then added and the stirring continued for 5 minutes. Sodium hydroxide solution (2M, 10 mL) was added and the resulting mixture was stirred at 20° C. for 30 minutes. The reaction mixture was then partitioned between dichloromethane (40 mL) and water (40 mL). The aqueous layer was acidified to pH 1 by the addition of hydrochloric acid (2M) and then extracted with dichloromethane (2×40 mL). The combined organic layers were dried and the solvent removed in vacuo to give the title compound as a yellow oil (612 mg).

LC retention time 2.55 mins. Mass spectrum m/z 553 [M⁻]

Experimental Data

Salmeterol xinafoate formulations in HFA 134a, of strength 25 µg per actuation, and 10% w/w (relative to drug) of the relevant surfactant compound of formula (I) were prepared in crimped glass bottles using salmeterol xinafoate (8.7 mg), HFA 134a (18 g) and the relevant compound (0.87 mg). The control was prepared without the addition of a surfactant. Table 1 shows mean particle size data determined by image analysis using a Galai CIS-100 particle size analyser for sample formulations prepared as described above. In this measurement, particle size is represented as the equivalent diameter of a circle of equal area to the object. The mean is the average of 4 determinations. The particle size measurement was obtained by transferring the suspensions to a pressurised cell, and video-imaging the sample under shear via a microscope objective. The equivalent diameter is defined as the diameter of a circle of equal area to the object.

$$\text{Equivalent Diameter} = \sqrt{\frac{\text{Area}}{\pi}}$$

The mean equivalent diameter can be weighted by number, length or volume. e.g. For three particles with equivalent diameters of x, y and z:

$$\text{Mean Number weighted diameter} = \left(\frac{1}{3}\right)x + \left(\frac{1}{3}\right)y + \left(\frac{1}{3}\right)z$$

$$\text{Mean Length weighted diameter} = \left(\frac{x}{x+y+z}\right)x + \left(\frac{y}{x+y+z}\right)y + \left(\frac{z}{x+y+z}\right)z$$

The data shows that compounds of formula (I) according to the invention have suspension stabilising properties thereby discouraging flocculation of drug particles. This is seen by the marked reduction in average particle size ("mean length") when a compound of formula (I) is incorporated into the formulation. Futhermore the spread of the range of particles size was reduced in some cases (especially Examples 5 and 7).

TABLE 1

Particle Size Data

| E.g. No. | Mean Length µm | Standard Deviation | Relative Standard Deviation |
|---|---|---|---|
| Control | 38.8 | 3.0 | 7.8 |
| 2 | 27.1 | 2.9 | 10.7 |
| 6 | 23.7 | 2.3 | 9.5 |
| 5 | 23.8 | 1.2 | 4.9 |
| 7 | 28.6 | 1.2 | 4.1 |

Table 2 shows data relating to the total drug emitted, drug emitted ex-device and the fine particle mass fraction (FPM the sum of stages 3 to 5) obtained using an Anderson Cascade Impactor stack. Data were obtained at the beginning of use of the device. Salmeterol xinafoate formulations in HFA 134a, of strength 25 µg per actuation, and 10% w/w (relative to drug) of the relevant surfactant compound of formula (I) were prepared in standard aluminum canisters. Control 1 was prepared at the same time as samples containing examples 2, 5, 6 and 7 whereas control 2 was prepared separately. The analysis of aerosol formulations using such stacks is well known to person skilled in the art. The results are presented as the mean of two determinations.

The table shows that the total emitted dose and the total emitted ex-device is increased for samples containing compounds of formula (I). These samples also show an increase in the absolute value of the FPM fraction in most cases. This indicates that a greater proportion of the dose will be available to reach the therapeutic target of in the lung which is desirable. Furthermore, advantageously the amount of overage, incorporated in the manufacturing process, to compensate for losses of the dose which is strictly regulated, may be reduced if more of the dose in dispensed as seen in the samples containing compounds of formula (I).

TABLE 2

Total & Ex-device Emitted Dose and FPM Data Using Cascade Impaction

| E.g. No. | Total Dose Emitted μg | Total Emitted Ex-Device μg | FPM μg | % FPM |
|---|---|---|---|---|
| Control 1 | 20.4 | 17.3 | 7.7 | 37.5 |
| Control 2 | 19.0 | 15.9 | 7.0 | 36.8 |
| 2 | 22.4 | 18.8 | 8.7 | 38.8 |
| 5 | 23.0 | 19.4 | 8.6 | 37.2 |
| 6 | 21.4 | 17.9 | 7.1 | 33.2 |
| 7 | 21.9 | 18.4 | 8.5 | 38.7 |

THE BRIEF DESCRIPTION OF DRAWING

FIG. 1 shows the mean cascade impaction profile of two determinations for salmeterol xinafoate 134a formulations containing Example 5, control 1 and control 2 the latter two being formulations which contain no surfactant.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A method for treating respiratory disorders comprising: administering to a patient a pharmaceutical aerosol formulation comprising: (i) a compound formula (I)

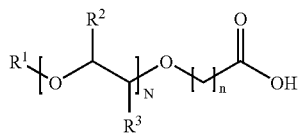

or a salt thereof, wherein;
n represents an integer 1 to 6;
N represents an integer 1 to 15;
wherein $R^1$ represents $C_{1-3}$ alkyl optionally substituted by up to 3 fluorine atoms; and
$R^2$ and $R^3$ independently represent $C_{1-3}$ alkyl or hydrogen,
(ii) at least one drug selected from the group consisting of antiallergics, anti-inflammatories, bronchodilators, anticholinergics, physiologically acceptable salts thereof, and physiologically acceptable esters thereof, and (iii) at least one propellant.

2. A method according to claim 1 wherein n represents an integer 1 to 4.

3. A method according to claim 1 wherein N represents an integer 1 to 8.

4. A method according to claim 1, wherein said compound is in the form of the free acid.

5. A method according to claim 1, wherein said at least one drug is selected from the group consisting of antiallergics, bronchodilators, anti-inflammatory steroids, physiologically acceptable salts thereof, and physiologically acceptable esters thereof.

6. A method according to claim 1, wherein said at least one drug is selected from the group consisting of cromoglycate, albuterol, salmeterol, formoterol, terbutaline, reproterol, beclomethasone, fluticasone, physiologically acceptable salts thereof, and physiologically acceptable esters thereof.

7. A method according to claim 1, wherein said at least one drug is albuterol sulphate.

8. A method according to claim 1, wherein said at least one drug is salmeterol xinafoate.

9. A method according to claim 1, wherein said at least one drug is a combination of fluticasone propionate and salmeterol xinafoate.

10. A method for treating respiratory disorders comprising:
administering to a patient a pharmaceutical aerosol formulation comprising: (i) a compound of formula (I)

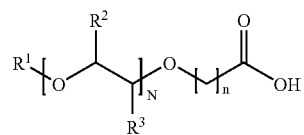

or a salt thereof, wherein:
n represents an integer 1 and 6;
N represents an integer 1 and 15;
wherein $R^1$ represents —$C_{5-6}$ alkylene $C_{1-3}$ fluoroalkyl; and
$R^2$ and $R^3$ independently represent $C_{1-3}$ alkyl or hydrogen,
(ii) at least one drug selected from the group consisting of antiallergics, anti-inflammatories, bronchodilators, anticholinergics, physiologically acceptable salts thereof, and physiologically acceptable esters thereof, and (iii) at least one propellant.

11. A method according to claim 10 wherein n represents an integer 1 to 4.

12. A method according to claim 10 wherein N represents an integer 1 to 8.

13. A method according to claim 10, wherein said compound is in the form of the free acid.

14. A method according to claim 10, wherein said at least one drug is selected from the group consisting of antiallergics, bronchodilators, anti-inflammatory steroids, physiologically acceptable salts thereof, and physiologically acceptable esters thereof.

15. A method according to claim 10, wherein said at least one drug is selected from the group consisting of cromoglycate, albuterol, salmeterol, formoterol, terbutaline, reproterol, beclomethasone, fluticasone, physiologically and acceptable salts thereof, and physiologically acceptable esters thereof.

16. A method according to claim 10, wherein said at least one drug is albuterol sulphate.

17. A method according to claim 10, wherein said at least one drug is salmeterol xinafoate.

18. A method according to claim 10, wherein said at least one drug is fluticasone propionate and salmeterol xinafoate.

19. A method for treating respiratory disorders comprising:
administering to a patient a pharmaceutical aerosol formulation comprising: (i) a compound selected from the group consisting of:
2,5,8,11-tetraoxatridecan-13-oic acid;
2,5,8,11,14,17,20-heptaoxadocosan-22-oic acid;
2,5,8,11-tetraoxahexadecan-16-oic acid;
2,5,8,11,14,17,20-heptaoxapentacosan-25-oic acid 23,23,23-trifluoro-3,6,9,12,15,18,21-heptaoxatricosan-1-oic acid;
{[2-({2-[2,2,2-trifluoroethyl)oxy]ethyl}oxy)ethyl]oxy}acetic acid;
2,5,8,11,14,17,20,23,26,29-decaoxaheritriacontan-3-oic acid;
25,25,26,26,26-pentafluoro-3,6,9,12,15,18,21-heptaoxahexacosan-1-oic acid;
(2-{2[(4,4,5,5,5-pentafluoropentyl)oxy]ethoxy}ethoxy)acetic acid;
{2-[2-(2,2,3,3,3-pentafluoropentyl)ethoxy]ethoxy}acetic acid;
23,23,24,24,24-pentafluoro-3,6,9,12,15,18,21-heptaoxatetracosan-1-oic acid;
32,32,32-trifluoro-3,6,9,12,15,18,21,24,27,30-decaoxadotriaconian-1-oic acid;
and physiologically acceptable salts thereof, and mixtures thereof; (ii) at least one drug selected from the group consisting of antiallergics, anti-flammatories, bronchodilators, anticholinergics, physiologically acceptable salts thereof, and physiologically acceptable esters thereof, and (iii) at least one propellant.

20. A method according to claim 19, wherein said at least one drug is selected from the group consisting of antiallergics, bronchodilators, anti-inflammatory steroids, physiologically acceptable salts thereof, and physiologically acceptable esters thereof.

21. A method according to claim 19, wherein said at least one drug is selected from the group consisting of cromoglycate, albuterol, salmeterol, formoterol, terbutaline, reproterol, beclomethasone, fluticasone, physiologically acceptable salts thereof, and physiologically acceptable esters thereof.

22. A method according to claim 19, wherein said at least one drug is albuterol sulphate.

23. A method according to claim 19, wherein said at least one drug is salmeterol xinafoate.

24. A method according to claim 19, wherein said at least one drug is fluticasone propionate and salmeterol xinafoate.

25. A method for treating respiratory disorders comprising:
administering to a patient a pharmaceutical aerosol formulation comprising: (i) a compound of formula (I)

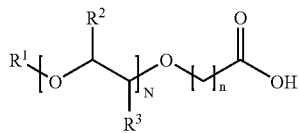

or a salt thereof, wherein:
n represents an integer 1 and 6;
N represents an integer 1 and 15;
$R^1$ represents $-(CO)_xC_{1-3}$ alkyl or $-(CO)_xC_{1-3}$ fluoroalkyl, which the number of fluorine atoms present in the fluoroalkyl moiety range from at least 1 fluorine atom to not more than 3 consecutive perfluorocarbon atoms wherein x represents 0 or 1; and
$R^2$ and $R^3$ independently represent $C_{1-3}$ alkyl or hydrogen,
(ii) at least one drug selected from the group consisting of antiallergics, anti-flammatories, bronchodilators, anticholinergics, physiologically acceptable salts thereof, and physiologically acceptable esters thereof, and (iii) at least one propellant selected from the group consisting of $CF_3CH_2F$, $CF_3CHFCF_3$ and mixtures thereof.

26. A method according to claim 25 wherein $R^1$ represents $-(CO)_xC_{1-6}$ alkyl or $-(CO)_xC_{1-6}$ fluoroalkyl, wherein the number of fluorine atoms present in the fluoroalkyl moiety range from at least 1 fluorine atom to not more than 3 consecutive perfluorocarbon atoms.

27. A method according to claim 25 wherein $R^1$ represents $-(CH_2)_3CF_2CF_3$, $-CH_2CF_2CF_3$, $-CH_2CF_3$, $-CF_2CF_3$ or $CH_3$.

28. A method according to claim 25 wherein $R^2$ and $R^3$ represent hydrogen.

29. A method according to claim 25 wherein x represents 0.

30. A method according to claim 25 wherein n represents an integer 1 to 4.

31. A method according to claim 25 wherein N represents an integer 1 to 8.

32. A method according to claim 25, wherein said compound is in the form of the free acid.

33. A method according to claim 25, wherein said at least one drug is selected from the group consisting of antiallergics, bronchodilators, anti-inflammatory steroids, physiologically acceptable salts thereof, and physiologically acceptable esters thereof.

34. A method according to claim 25, wherein said at least one drug is selected from the group consisting of cromoglycate, albuterol, salmeterol, formoterol, terbutaline, reproterol, beclomethasone, fluticasone, physiologically acceptable salts thereof, and physiologically acceptable esters thereof.

35. A method according to claim 25, wherein said at least one drug is albuterol sulphate.

36. A method according to claim 25, wherein said at least one drug is salmeterol xinafoate.

37. A method according to claim 25, wherein said at least one drug is fluticasone propionate and salmeterol xinafoate.

38. A method according to claim 1 wherein said at least one propellant is selected from the group consisting of $CHF_2CHF_2$, $CF_3CH_2F$, $CHF_2CH_3$, $CF_3CHFCF_3$, $CF_3CF_3$, $CF_3CF_2CF_3$, and mixtures thereof.

39. A method according to claim 1, wherein said at least one propellant is $CF_3CH_2F$.

40. A method according to claim 1, wherein said at least one propellant is $CF_3CHFCF_3$.

41. A method according to claim 10, wherein said at least one propellant is selected from the group consisting of $CHF_2CHF_2$, $CF_3CH_2F$, $CHF_2CH_3$, $CF_3CHFCF_3$, $CF_3CF_3$, $CF_3CF_2CF_3$, and mixtures thereof.

42. A method according to claim 10, wherein said at least one propellant is $CF_3CH_2F$.

43. A method according to claim 10, wherein said at least one propellant is $CF_3CHFCF_3$.

44. A method according to claim 19, wherein said at least one propellant is selected from the group consisting of $CHF_2CHF_2$, $CF_3CH_2F$, $CHF_2CH_3$, $CF_3CHFCF_3$, $CF_3CF_3$, $CF_3CF_2CF_3$, and mixtures thereof.

45. A method according to claim 19, wherein said at least one propellant is $CF_3CH_2F$.

46. A method according to claim 19, wherein said at least one propellant is $CF_3CHFCF_3$.

* * * * *

UNITED STATES PATENT AND TRADEMARK OFFICE
CERTIFICATE OF CORRECTION

PATENT NO.       : 7,217,409 B2
APPLICATION NO.  : 10/381116
DATED            : May 15, 2007
INVENTOR(S)      : Brian Edgar Looker et al.

It is certified that error appears in the above-identified patent and that said Letters Patent is hereby corrected as shown below:

Correction to the Title: The title should read
-- NOVEL ALKANOIC ACID DERIVATIVES --

Correction to FOREIGN PATENT DOCUMENTS:
-- DD       258179       7/1988 --

Correction to OTHER PUBLICATIONS:

Database WPI should read
-- Database WPI, Section Ch, Week 200027, Derwent Publications Ltd., London, GB; Class A96, AN 2000-312984 & JP2000095726A (Kawaken Fine Chem Co. Ltd.), Apr. 4, 2000 abstract. --

Corrections to the Claims:

Claim 1 - Column 19, Line 32 - should read
-- formulation comprising: (i) a compound of formula (I) --

Claim 10 - Column 20, Line 25, 26 and 27 - should read
-- n represents an integer 1 to 6; --
-- N represents an integer 1 to 15; --
-- wherein R1 represents –C0-6 alkylene C1-3 fluoroalkyl; --

Claim 18 - Column 20, Line 58 - should read
-- one drug is a combination of fluticasone propionate and salmeterol xinafoate. --

Claim 19 - Column 21, Line 5 - should read
-- 2,5,8,11,14,17,20,23,26,29-decaoxahentriacontan-31-oic acid --

Claim 19 - Column 21, Lines 11-12 - should read
-- {2-[2-(2,2,3,3,3-pentafluoropropoxy)ethoxy]ethoxy}acetic acid--

Claim 19 - Column 21, Line 16 - should read
-- decaoxadotriacontan-1-oic acid --

Claim 19 - Column 21, Line 19 - should read
-- consisting of antiallergics, anti-inflammatories, bronchodilators, --

Claim 24 - Column 21, Line 39 - should read
-- one drug is a combination of fluticasone propionate and salmeterol xinafoate. --

UNITED STATES PATENT AND TRADEMARK OFFICE
CERTIFICATE OF CORRECTION

PATENT NO. : 7,217,409 B2
APPLICATION NO. : 10/381116
DATED : May 15, 2007
INVENTOR(S) : Brian Edgar Looker et al.

It is certified that error appears in the above-identified patent and that said Letters Patent is hereby corrected as shown below:

Claim 25 - Column 21, Lines 54, 55 and 56 - should read
-- n represents an integer 1 to 6; --
-- N represents an integer 1 to 15; --
-- R1 represents -(CO)xC1-9 alkyl or -(CO)xC1-9 fluoroalkyl, --

Claim 26 - Column 22, Line 5 - should read
-- -(CO)xC1-5 alkyl or -(CO)xC1-5 fluoroalkyl, wherein the --

Claim 26 - Column 22, Line 7 - should read
-- ranges from at least 1 fluorine atom to not more than 3 --

Claim 37 - Column 22, Line 38 - should read
-- one drug is a combination of fluticasone propionate and salmeterol xinafoate. --

Signed and Sealed this

Thirteenth Day of November, 2007

JON W. DUDAS
*Director of the United States Patent and Trademark Office*